United States Patent
Sung et al.

(10) Patent No.: US 11,111,340 B2
(45) Date of Patent: Sep. 7, 2021

(54) METHOD FOR PREPARING BIOCOMPATIBLE POLY-γ-GLUTAMIC ACID HYDROGEL BY USING ULTRAVIOLET RAYS

(71) Applicant: KOOKMIN UNIVERSITY INDUSTRY ACADEMY COOPERATION FOUNDATION, Seoul (KR)

(72) Inventors: Moon Hee Sung, Seoul (KR); Misun Kwak, Goyang-si (KR); Sang Joon Park, Yangju-si (KR)

(73) Assignee: KOOKMIN UNIVERSITY INDUSTRY ACADEMY COOPERATION FOUNDATION, Seoul (KR)

( * ) Notice: Subject to any disclaimer, the term of this patent is extended or adjusted under 35 U.S.C. 154(b) by 0 days.

(21) Appl. No.: 17/255,422

(22) PCT Filed: May 9, 2019

(86) PCT No.: PCT/KR2019/005586
§ 371 (c)(1),
(2) Date: Dec. 22, 2020

(87) PCT Pub. No.: WO2020/004810
PCT Pub. Date: Jan. 2, 2020

(65) Prior Publication Data
US 2021/0139655 A1    May 13, 2021

(30) Foreign Application Priority Data

Jun. 26, 2018 (KR) .......................... 10-2018-0073512
Feb. 26, 2019 (KR) .......................... 10-2019-0022446

(51) Int. Cl.
| | | |
|---|---|---|
| *C08F 283/04* | (2006.01) |
| *C08G 69/48* | (2006.01) |
| *C08L 77/00* | (2006.01) |
| *C08F 2/46* | (2006.01) |
| *C08F 2/50* | (2006.01) |
| *C08G 61/04* | (2006.01) |
| *C08J 3/075* | (2006.01) |
| *A61K 8/88* | (2006.01) |
| *A61L 27/18* | (2006.01) |
| *A61Q 19/00* | (2006.01) |
| *C08J 3/24* | (2006.01) |
| *C08J 3/28* | (2006.01) |

(52) U.S. Cl.
CPC ............ *C08J 3/075* (2013.01); *A61K 8/88* (2013.01); *A61L 27/18* (2013.01); *A61Q 19/00* (2013.01); *C08G 69/48* (2013.01); *C08J 3/24* (2013.01); *C08J 3/28* (2013.01); *C08J 2477/04* (2013.01)

(58) Field of Classification Search
CPC .. C08F 2/46; C08F 2/50; C08F 283/04; C08F 283/00; C08F 290/14; C08G 61/04; C08G 69/48; C08G 63/91; C08G 63/48
USPC ...................... 522/421, 420, 419, 418; 520/1
See application file for complete search history.

(56) References Cited

U.S. PATENT DOCUMENTS

2008/0003571 A1    1/2008  McKernan et al.

FOREIGN PATENT DOCUMENTS

| CN | 108192034 | * | 6/2018 | |
| JP | 2007-112785 A | | 5/2007 | |
| KR | 10-0496606 B1 | | 6/2005 | |
| KR | 10-2010-0000040 A | | 1/2010 | |
| KR | 10-2014-0001686 A | | 1/2014 | |
| WO | WO-2014156709 A1 | * | 10/2014 | ............ D06M 15/27 |

OTHER PUBLICATIONS

Imao et al, WO 2014/156709 Machine Translation, Oct. 2, 2014 (Year: 2014).*
Chi et al, CN 108192034 Machine Translation, Jun. 22, 2018 (Year: 2018).*
International Search Report for PCT/KR2019/005586 dated Aug. 21, 2019 from Korean Intellectual Property Office.
Bako, Jozsef et al., "Poly-gamma-Glutamic Acid Nanoparticles Based Visible Light-Curable Hydrogel for Biomedical Application", Journal of Nanomaterials, vol. 2016, Article ID 7350516, 10 pages.
Fan, Zhiping et al., "Poly(glutamic acid) hydrogels crosslinked via native chemical ligation", New J. Chem., 2017, 41, 8656-8662.
Luana Becker Peres et al., "pH-responsive physically and chemically cross-linked glutamic-acid-based hydrogels and nanogels", European Polymer Journal 101 (2018) 341-349.
Hyuk Joon Choi et al., "Preparation conditions and swelling equilibria of hydrogel prepared by γ-irradiation from microbial poly(γ-glutamic acid)", Radiation Physics and Chemistry, vol. 46, Issue 2, Aug. 1995, pp. 175-179.

* cited by examiner

*Primary Examiner* — Jessica Whiteley
(74) *Attorney, Agent, or Firm* — Revolution IP, PLLC

(57) ABSTRACT

The present invention relates to a method of preparing a poly-γ-glutamic acid hydrogel using ultraviolet ray and to a use of the poly-γ-glutamic acid hydrogel prepared by the method, and the method of preparing poly-γ-glutamic acid hydrogel using ultraviolet irradiation according to the present invention solved the problem of microbial contamination in the poly-γ-glutamic acid solution, and produced poly-γ-glutamic acid hydrogel in high yield by only a simple treatment process, and as it was confirmed that the poly-γ-glutamic acid hydrogel has improved storage stability in a solution, the poly-gamma-glutamic acid hydrogel prepared by the method of preparing the same of the present invention can be provided as a tissue engineering scaffold, artificial organs and bio-ink for 3D printing.

6 Claims, 4 Drawing Sheets

[FIG. 1]
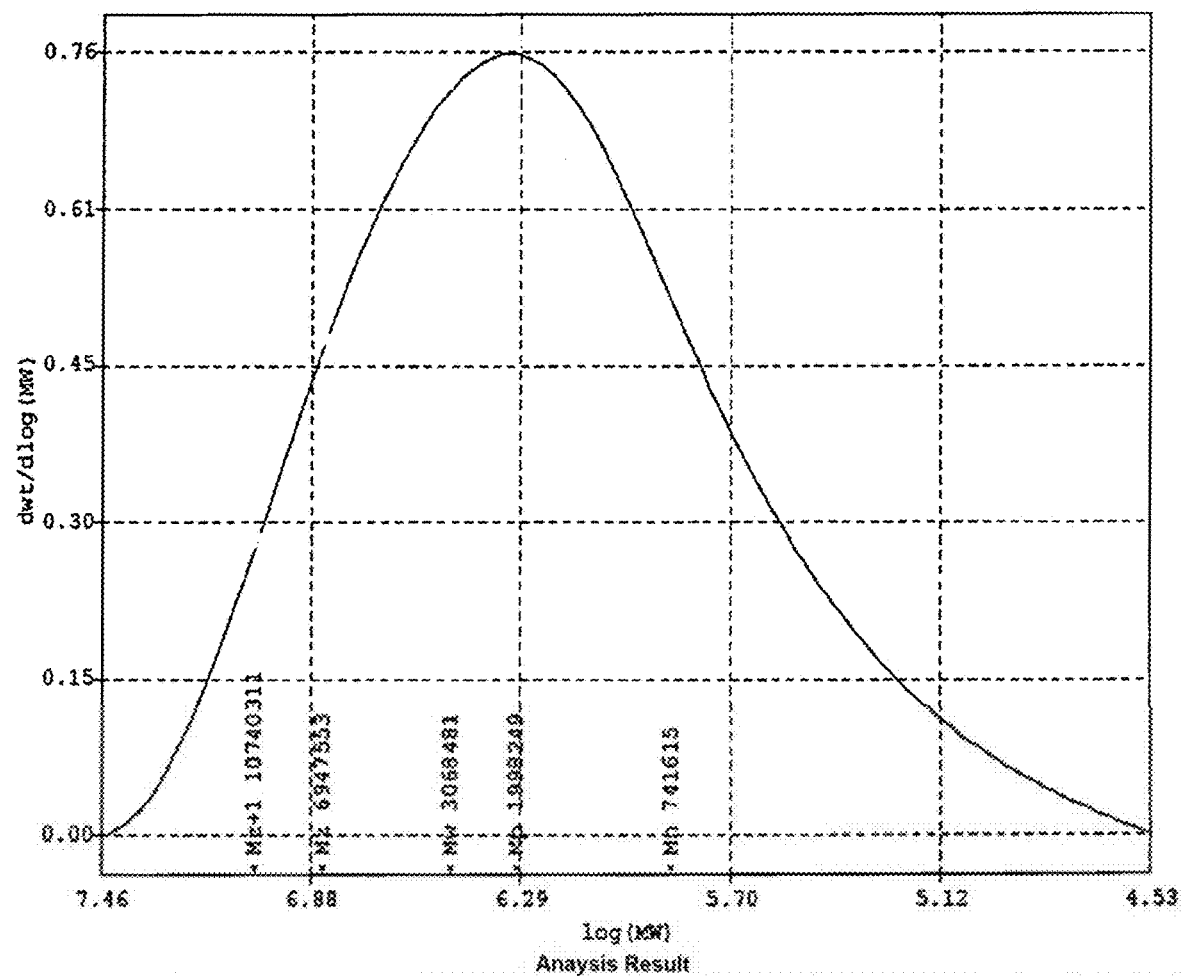

[FIG. 2]

| No. | Detection time (min) | Molecular weight (Da) | No. | Detection time (min) | Molecular weight (Da) |
|---|---|---|---|---|---|
| 1 | 7.67 | 28,939,410 | 51 | 9.33 | 998,439 |
| 2 | 7.70 | 27,527,628 | 52 | 9.37 | 923,522 |
| 3 | 7.73 | 26,158,942 | 53 | 9.40 | 854,124 |
| 4 | 7.77 | 24,834,301 | 54 | 9.43 | 789,862 |
| 5 | 7.80 | 23,554,357 | 55 | 9.47 | 730,374 |
| 6 | 7.83 | 22,319,541 | 56 | 9.50 | 675,322 |
| 7 | 7.87 | 21,130,147 | 57 | 9.53 | 624,389 |
| 8 | 7.90 | 19,986,178 | 58 | 9.57 | 577,280 |
| 9 | 7.93 | 18,887,523 | 59 | 9.60 | 533,717 |
| 10 | 7.97 | 17,833,846 | 60 | 9.63 | 493,443 |
| 11 | 8.00 | 16,824,738 | 61 | 9.67 | 456,218 |
| 12 | 8.03 | 15,859,578 | 62 | 9.70 | 421,817 |
| 13 | 8.07 | 14,937,859 | 63 | 9.73 | 390,032 |
| 14 | 8.10 | 14,058,182 | 64 | 9.77 | 360,668 |
| 15 | 8.13 | 13,220,220 | 65 | 9.80 | 333,545 |
| 16 | 8.17 | 12,422,764 | 66 | 9.83 | 308,494 |
| 17 | 8.20 | 11,664,763 | 67 | 9.87 | 285,361 |
| 18 | 8.23 | 10,945,079 | 68 | 9.90 | 264,000 |
| 19 | 8.27 | 10,262,549 | 69 | 9.93 | 244,276 |
| 20 | 8.30 | 9,615,938 | 70 | 9.97 | 226,066 |
| 21 | 8.33 | 9,004,016 | 71 | 10.00 | 209,255 |
| 22 | 8.37 | 8,425,510 | 72 | 10.03 | 193,734 |
| 23 | 8.40 | 7,879,154 | 73 | 10.07 | 179,406 |
| 24 | 8.43 | 7,363,649 | 74 | 10.10 | 166,178 |
| 25 | 8.47 | 6,877,732 | 75 | 10.13 | 153,966 |
| 26 | 8.50 | 6,420,114 | 76 | 10.17 | 142,691 |
| 27 | 8.53 | 5,989,538 | 77 | 10.20 | 132,282 |
| 28 | 8.57 | 5,584,759 | 78 | 10.23 | 122,670 |
| 29 | 8.60 | 5,204,564 | 79 | 10.27 | 113,795 |
| 30 | 8.63 | 4,847,744 | 80 | 10.30 | 105,599 |
| 31 | 8.67 | 4,513,132 | 81 | 10.33 | 98,029 |
| 32 | 8.70 | 4,199,596 | 82 | 10.37 | 91,037 |
| 33 | 8.73 | 3,906,028 | 83 | 10.40 | 84,577 |
| 34 | 8.77 | 3,631,354 | 84 | 10.43 | 78,609 |
| 35 | 8.80 | 3,374,546 | 85 | 10.46 | 74,432 |
| 36 | 8.83 | 3,134,699 | 86 | 10.48 | 70,495 |
| 37 | 8.87 | 2,910,578 | 87 | 10.51 | 66,783 |
| 38 | 8.90 | 2,701,540 | 88 | 10.53 | 63,284 |
| 39 | 8.93 | 2,506,611 | 89 | 10.56 | 59,985 |
| 40 | 8.97 | 2,324,949 | 90 | 10.58 | 56,874 |
| 41 | 9.00 | 2,155,751 | 91 | 10.61 | 53,939 |
| 42 | 9.03 | 1,998,249 | 92 | 10.63 | 51,172 |
| 43 | 9.07 | 1,851,715 | 93 | 10.66 | 48,561 |
| 44 | 9.10 | 1,715,456 | 94 | 10.68 | 46,097 |
| 45 | 9.13 | 1,588,817 | 95 | 10.71 | 43,773 |
| 46 | 9.17 | 1,471,175 | 96 | 10.73 | 41,579 |
| 47 | 9.20 | 1,361,941 | 97 | 10.76 | 39,508 |
| 48 | 9.23 | 1,260,561 | 98 | 10.78 | 37,554 |
| 49 | 9.27 | 1,166,508 | 99 | 10.81 | 35,708 |
| 50 | 9.30 | 1,079,290 | 100 | 10.83 | 33,965 |

[FIG. 3]
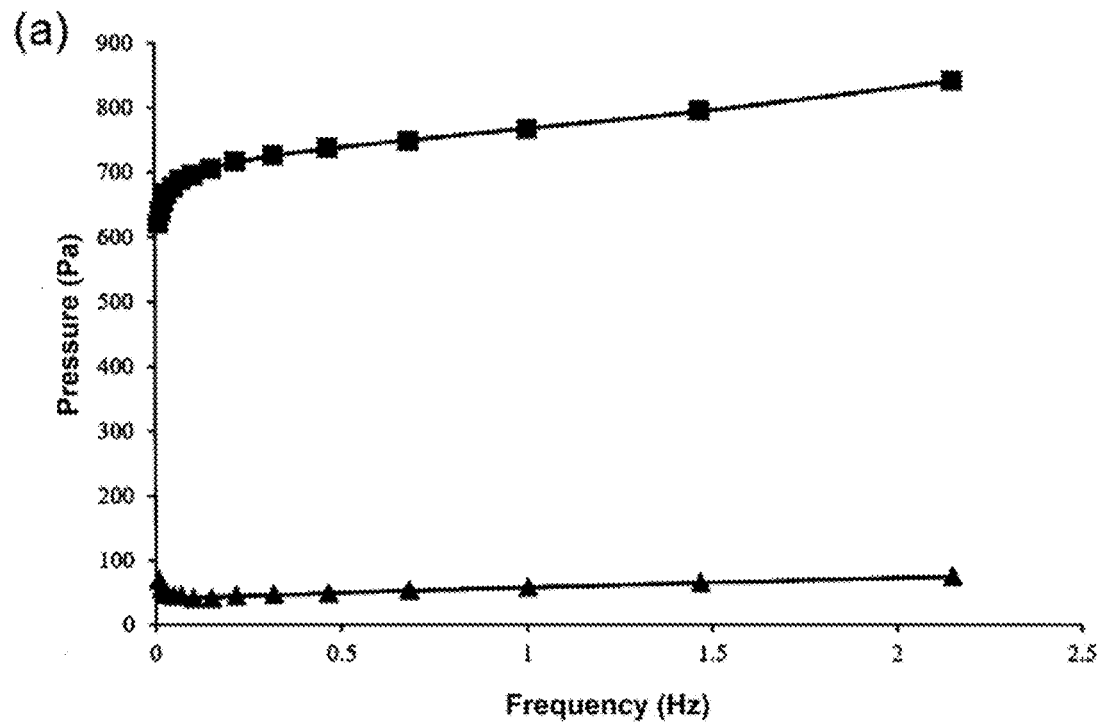
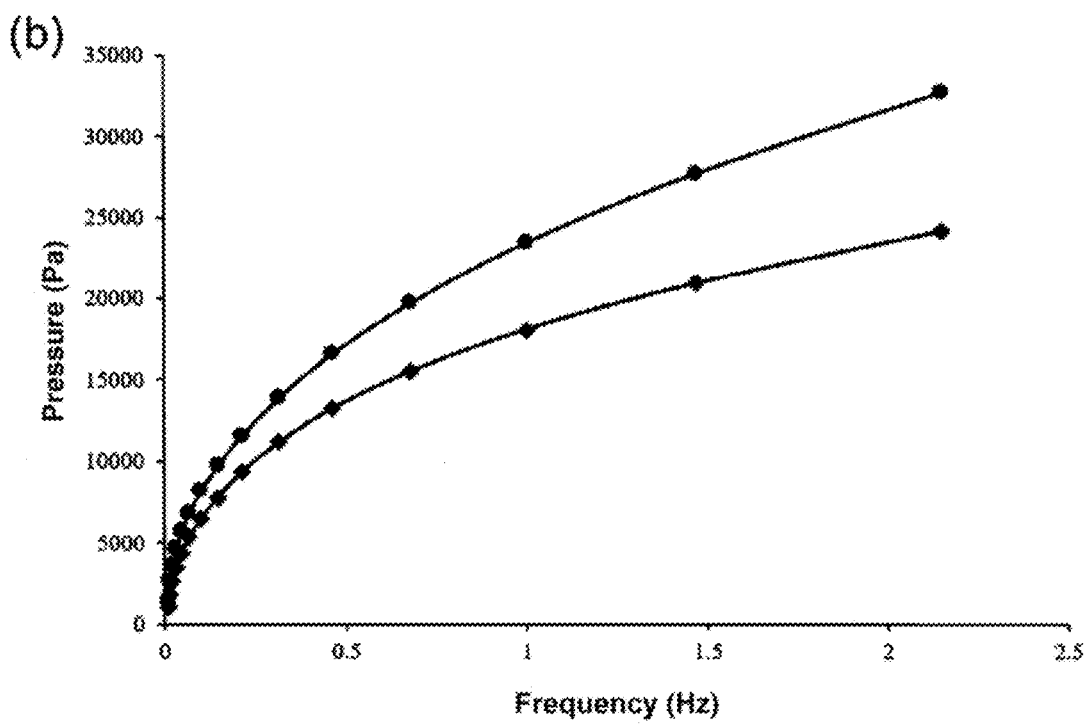

| Solution | Day 0 | Week 1 | Week 2 | Week 3 | Week 4 | Week 5 | Week 6 | Week 7 | Week 8 | Week 9 | Week 10 |
|---|---|---|---|---|---|---|---|---|---|---|---|
| Distilled water | | | | | | | | | | | |
| 20mM Potassium phosphate buffer solution (pH 6.0) | | | | | | | | | | | |
| 0.9% sodium chloride solution | | | | | | | | | | | |
| Phosphate buffered saline | | | | | | | | | | | |
| Artificial body fluid | | | | | | | | | | | |

(b)

| Solution | Day 0 | Week 1 | Week 2 | Week 3 | Week 4 | Week 5 | Week 6 | Week 7 | Week 8 | Week 9 | Week 10 |
|---|---|---|---|---|---|---|---|---|---|---|---|
| Distilled water | | | | | | | | | | | |
| 20mM Potassium phosphate buffer solution (pH 6.0) | | | | | | | | | | | |
| 0.9% sodium chloride solution | | | | | | | | | | | |
| Phosphate buffered saline | | | | | | | | | | | |
| Artificial body fluid | | | | | | | | | | | |

METHOD FOR PREPARING BIOCOMPATIBLE POLY-γ-GLUTAMIC ACID HYDROGEL BY USING ULTRAVIOLET RAYS

CROSS REFERENCE TO PRIOR APPLICATIONS

This application is the 35 U.S.C. 371 national stage of International application PCT/KR2019/005586 filed on May 9, 2019; which claims priority to Korean application 10-2018-0073512 filed on Jun. 26, 2018, and Korean application 10-2019-0022446 filed on Feb. 26, 2019. The entire contents of each of the above-identified applications are hereby incorporated by reference.

TECHNICAL FIELD

The present invention relates to a method of preparing poly-γ-glutamic acid hydrogel using ultraviolet light, and to a use of a biocompatible poly-γ-glutamic acid hydrogel prepared by the method.

BACKGROUND ART

Hydrogel generally refers to a material having a three-dimensional hydrophilic polymer network that contains a large amount of water, and is made of a homopolymer or a copolymer, and forms a structurally stable three-dimensional structure with little induction by external force. As this structure is formed by various factors such as hydrogen bonds, covalent bonds, or physical aggregation, hydrogels are thermodynamically stable after swelling in an aqueous solution, and have mechanical and physicochemical properties corresponding to an intermediate form between a liquid and a solid.

In addition, the swelling degree of the hydrogel can be adjusted according to the chemical structure of the polymer and the degree of crosslinking between the hydrophilicity and the polymer chain, thus it is possible to manufacture a hydrogel having various shapes and properties depending on the composition and preparation method. So far, many studies have been conducted on the physicochemical properties of hydrogels, and as a result, various types of hydrogels have been developed.

Hydrogel has been applied in the industry as a cosmetic material, starting with hygiene products based mainly on superabsorbent properties, and currently, it is usefully used in a very wide range of fields ranging from pharmaceutical applications such as drug delivery systems, embolization, tissue engineering scaffolds, and cosmetic fillers to industrial applications, with the introduction of various additional functions.

Poly-γ-glutamic acid is a material having a gamma-peptide bond and it is a natural amino acid polymer material produced from GRAS (Generally Recognized As Safe) such as *Bacillus subtilis*. Various studies on the development of hydrogels according to changes in the properties of poly-gamma-glutamic acid during gamma-ray irradiation and using crosslinking agents and their industrialization are being conducted in various ways.

However, as the poly-γ-glutamic acid hydrogel is observed to swell and dissolve in a solution such as water or a buffer solution, there is a need for research and development on biocompatible poly-γ-glutamic acid hydrogel that maintains its shape in a solution and exists in a stable state.

DISCLOSURE

Technical Problem

As described above, conventional poly-γ-glutamic acid hydrogel crosslinked by gamma-ray irradiation has a problem in that it swells and dissolves in a solution and thus in order to solve the hydrogel toxicity problem according to the chemical cross-linking method, the present invention is to provide a method of preparing a poly-γ-glutamic acid hydrogel cross-linked by using ultraviolet irradiation.

Technical Solution

The present invention provides a method of preparing poly-γ-glutamic acid hydrogel comprising: dissolving poly-γ-glutamic acid in a solvent (Step 1); adding and dissolving N,N,N-trimethyl-3-[(2-methylacryloyl)amino]propane-1-aminium to solution of the poly-γ-glutamic acid of the Step 1 (Step 2); and irradiating the solution of the Step 2 with ultraviolet rays (Step 3).

The present invention provides a poly-γ-glutamic acid hydrogel prepared by the above method of preparing the same.

The present invention provides a tissue engineering scaffold comprising the poly-γ-glutamic acid hydrogel.

The present invention provides an artificial organ comprising the poly-γ-glutamic acid hydrogel.

In addition, the present invention provides a bio-ink composition for a 3D printer comprising the poly-γ-glutamic acid hydrogel.

Advantageous Effects

According to the present invention, the method of preparing poly-γ-glutamic acid hydrogel using ultraviolet irradiation solves the problem of microbial contamination in the poly-γ-glutamic acid solution, and produces poly-γ-glutamic acid hydrogel in high yield by only a simple treatment process, and as it was confirmed that the poly-γ-glutamic acid hydrogel has improved storage stability in a solution, the poly-gamma-glutamic acid hydrogel prepared by the method of preparing the same of the present invention can be provided as a tissue engineering scaffold, artificial organs, and bio-ink for 3D printing.

DESCRIPTION OF DRAWINGS

FIG. 1 shows a chromatogram of gel permeation chromatography (GPC) analysis of poly-γ-glutamic acid used in the present invention.

FIG. 2 shows the molecular weight distribution of gel permeation chromatography (GPC) analysis of poly-γ-glutamic acid used in the present invention.

FIG. 3 is a graph showing the results of checking the viscoelasticity of the poly-γ-glutamic acid hydrogel irradiated with gamma rays (a), and the results of checking the viscoelasticity of the poly-γ-glutamic acid hydrogel according to the present invention (b).

FIG. 4 is an image showing the stability observation results of the poly-γ-glutamic acid hydrogel in solution irradiated with gamma rays (a), and the poly-γ-glutamic acid hydrogel in solution irradiated with ultraviolet ray according to the present invention in solution.

BEST MODE

Hereinafter, the present invention will be described in detail.

The inventors of the present invention have conducted research to improve the stability in solution of poly-γ-glutamic acid hydrogel and confirmed that a method of preparing a hydrogel using ultraviolet irradiation can produce poly-γ-glutamic acid hydrogel with high yield without treatment process such as recovery process and can solve the problem of microbial contamination in the poly-γ-glutamic acid solution and has the effect of improving the storage stability in the solution of the poly-γ-glutamic acid hydrogel, and completed the present invention.

The present invention can provide a method of preparing poly-γ-glutamic acid hydrogel comprising: dissolving poly-γ-glutamic acid in a solvent (Step 1); adding and dissolving N,N,N-trimethyl-3-[(2-methylacryloyl)amino]propane-1-aminium to solution of the poly-γ-glutamic acid of the Step 1 (Step 2); and irradiating the solution of the Step 2 with ultraviolet rays (Step 3).

In more detail, the poly-γ-glutamic acid may have a weight average molecular weight of 30 to 30,000 kDa, more preferably 33,965 to 28,939,415 Da, but it is not limited thereto.

In addition, the poly-γ-glutamic acid may be included in a solvent at 10 to 30 w/v %, more preferably 20 w/v %.

The solvent in the Step 1 may be water.

The N,N,N-trimethyl-3-[(2-methylacryloyl)amino]propane-1-aminium of the Step 2 may be added at a molecular ratio of 1:1 with respect to molecule number of glutamic acid, which is a poly-γ-glutamic acid monomer.

More specifically, when N,N,N-trimethyl-3-[(2-methylacryloyl)amino]propane-1-aminium is added below the addition ratio, the hydrogel properties are lowered and thus normal hydrogel cannot be generated.

In the Step 3 of irradiating ultraviolet rays, ultraviolet rays having an energy amount of 50 to 70 $mW/cm^2$ may be irradiated to the solution of the Step 2.

More specifically, the distance from the ultraviolet irradiator to the solution may be 30 cm, and irradiation may be performed for 2 hours at 365 nm ultraviolet wavelength. At this time, the amount of irradiated energy may be 50 to 70 $mW/cm^2$.

When ultraviolet rays are irradiated to a solution in which poly-γ-glutamic acid and N,N,N-trimethyl-3-[(2-methylacryloyl)amino]propane-1-aminium are mixed, the N,N,N-trimethyl-3-[(2-methylacryloyl)amino]propane-1-aminium is bonded to poly-γ-glutamic acid, and cross-linking between poly-γ-glutamic acid molecules occurs and as a result, poly-γ-glutamic acid hydrogel can be produced.

In addition, the method of preparing hydrogel may further comprise air-drying the solution irradiated with ultraviolet rays in the Step 3 at room temperature.

The poly-γ-glutamic acid hydrogel may be included in an artificial organ, tissue engineering scaffold, cosmetic material or a bio-ink composition for 3D printers with improved storage stability and viscoelasticity.

The present invention can provide a poly-γ-glutamic acid hydrogel according to the method of preparing the poly-γ-glutamic acid hydrogel.

The poly-γ-glutamic acid hydrogel may have improved storage stability and viscoelasticity.

According to an embodiment of the present invention, in order to confirm the stability in a solution of the poly-γ-glutamic acid hydrogel prepared through ultraviolet irradiation or gamma ray irradiation, a change in the form of the hydrogel over time was confirmed. 3 g of poly-γ-glutamic acid hydrogel prepared by the above method before air-drying was placed in a petri dish and air-dried to prepare a circular gel and each of distilled water, 20 mM potassium phosphate buffer (KPB; pH 6.0), 1×PBS, 0.9% sodium chloride (NaCl) solution and artificial body fluid were poured into gel so that the gel was immersed, and then left to stand at a humidity of 60% and a temperature of 25° C. to confirm the change in shape over time. Poly-γ-glutamic acid hydrogel prepared by irradiating gamma rays in the same manner as the above was placed in a petri dish, freeze-dried and crushed, and then the shape change over time was confirmed in the various solutions.

As a result, it was confirmed that the poly-γ-glutamic acid hydrogel prepared by ultraviolet irradiation as shown in FIG. 4 was maintained in shape for 8 weeks, whereas the poly-γ-glutamic acid hydrogel prepared by gamma ray irradiation was expanded and dissolved.

From the above results, it was confirmed that the air-dried poly-γ-glutamic acid hydrogel after UV irradiation maintained stability for a long time even in a solution.

Accordingly, the present invention can provide a tissue engineering scaffold and an artificial organ comprising poly-γ-glutamic acid hydrogel with improved storage stability.

The artificial organ may be selected from the group consisting of artificial skin, artificial cornea, artificial blood vessel, artificial urethra, artificial small intestine, artificial bronchi, artificial liver, artificial kidney, artificial bone, artificial peripheral and central nerves, artificial bladder, artificial tendon and artificial cartilage, but it is not limited thereto.

In addition, the present invention may provide a bio-ink composition for a 3D printer comprising the poly-γ-glutamic acid hydrogel.

Hereinafter, examples will be described in detail to aid understanding of the present invention. However, the following examples are only intended to illustrate the present invention and the scope of the present invention is not limited to the following examples. The examples of the present invention are provided to more completely explain the present invention to those skilled in the art.

The following reference examples are intended to provide reference examples commonly applied to each example according to the present invention.

<Reference Example> Experimental Material

Poly-γ-glutamic acid having a molecular weight of 3,965 Da to 28,939,415 Da used in the present invention (FIG. 1 and FIG. 2) was purchased from Bioleaders (Daejeon, Korea), and its lot number is F1PB0316FK.

N,N,N-trimethyl-3-[(2-methylacryloyl)amino]propan-1-aminium (Cat. No. 323-22842) was purchased from Wako Pure Chemical Industries. Ltd. (Japan) and its molecular weight is 220.74.

<Example 1> Preparation of Poly-γ-Glutamic Acid Hydrogel

1. Preparation of Poly-γ-Glutamic Acid Solution

After adding 30 ml of distilled water into a 100 ml screw vial, inserting a magnetic bar, and accurately weighing 10 g of poly-γ-glutamic acid (molecular weight from 3,965 Da to 28,939,415 Da) using a microbalance and placing it in the screw vial, the volume of the solution is adjusted to 50 ml and the mixture was dissolved by stirring at room temperature for 24 hours at a stirring speed of 300 rpm.

Thereafter, 17.11 g of N,N,N-trimethyl-3-[(2-methylacryloyl)amino]propane-1-aminium, which is the amount calculated by calculating a molecular ratio of 1:1 according to the number of molecules of glutamic acid, a monomer of poly-gamma-glutamic acid, present in poly-gamma-glutamic acid, was weighed with a microbalance, added and then dissolved while stirring at room temperature for 24 hours at a stirring speed of 300 rpm to prepare a 20 w/v % poly-γ-glutamic acid solution.

2. Preparation of Poly-γ-Glutamic Acid Hydrogel Through UV Irradiation and Drying Process The 20 w/v % poly-γ-glutamic acid solution prepared in Example 1 was irradiated with ultraviolet rays to prepare a hydrogel. During UV irradiation, the frame was assembled using two glass plates and rubber, and the 20 w/v % poly-γ-glutamic acid solution prepared in Example 1 was injected into the inside of the frame using a syringe, and then UV was irradiated.

UV rays of 365 nm wavelength were irradiated for 2 hours with a UV irradiator and a 15 cm clearance. The amount of energy irradiated at this time was 50-70 mW/cm$^2$. The thus prepared high viscosity solution was transferred to a petri dish and air-dried at room temperature to prepare a gel-shaped hydrogel.

<Comparative Example 1> Preparation of Gamma-Ray Irradiated Poly-γ-Glutamic Acid Hydrogel $KH_2PO_4$ was added to a 5 w/v % solution of poly-γ-glutamic acid so as to be 0.1 w/v %, and a gamma-ray-irradiated poly-gamma-glutamic acid hydrogel was prepared by irradiating gamma rays at a dose of 20 kGy.

<Example 2> Confirmation of Viscoelasticity of UV-Irradiated Poly-γ-Glutamic Acid Hydrogel The viscoelasticity of the poly-γ-glutamic acid hydrogel prepared by irradiating with ultraviolet rays and gamma rays of Example 1 and Comparative Example 1 was confirmed using a rheometer.

The viscoelasticity of 10 ml of air-dried hydrogel was measured with a gap of 0.8 mm at 25 points from 0.01 Hz to 100 Hz.

As a result, as shown in FIG. 3, the UV-irradiated poly-γ-glutamic acid hydrogel exhibited high viscosity and elasticity at all Hz, and particularly, the viscosity was higher than the elasticity in the range of 0.01 Hz to 10 Hz, whereas it was confirmed that the poly-γ-glutamic acid hydrogel irradiated with gamma-rays was significantly inferior in viscosity and elasticity, and thus it was confirmed that the ultraviolet-irradiated poly-γ-glutamic acid hydrogel prepared by the above method exhibited the characteristics of the gel.

<Example 3> Confirmation of Particle Diameter of Poly-γ-Glutamic Acid Hydrogel Molecule 1 g of poly-γ-glutamic acid powder prepared by lyophilizing and grinding the prepared poly-γ-glutamic acid hydrogel was weighed using a microbalance, and then dissolved in distilled water to make a final volume of 10 ml to prepare a 1% poly-γ-glutamic acid hydrogel solution. The prepared 1% poly-γ-glutamic acid hydrogel solution was treated with an ultrasonic wave using an ultrasonic processor at an output of 30% for a treatment time of 1 minute, an operation time of 1 second, and a break time of 2 seconds. 2 ml of the prepared solution was taken and the particle diameter of the poly-γ-glutamic acid hydrogel molecule was measured using a particle diameter measuring device.

As a result, the particle diameter of the poly-γ-glutamic acid hydrogel molecule was confirmed to be 1054.0±243.9 nm.

<Example 4> Confirmation of Surface Potential and Free Carboxyl Group of Poly-γ-Glutamic Acid Hydrogel Molecule 1 g of poly-γ-glutamic glutamic acid powder prepared by lyophilizing and grinding the poly-γ-glutamic acid hydrogel prepared in the Example 1 and the Comparative Example 1 was weighed using a microbalance and dissolved in distilled water to make a final volume of 10 ml to prepare a 1% poly-γ-glutamic acid hydrogel solution. The prepared 1% poly-γ-glutamic acid hydrogel solution was treated with an ultrasonic wave using an ultrasonic processor at an output of 30% for a treatment time of 1 minute, an operation time of 1 second, and a break time of 2 seconds. 2 ml of the prepared solution was taken and the surface potential of the poly-γ-glutamic acid hydrogel molecule was measured using a surface potential measuring device. All experimental groups were titrated to pH 4.8, which is the pKa of polyglutamic acid (PGA). In the experiment, a 1 μmol/ml poly-γ-glutamic acid solution of pH 4.8 was used as a control.

As a result, as shown in Table 1 below, the surface potential of the ultraviolet-irradiated poly-γ-glutamic acid hydrogel molecule was 29.30±0.77 mV, and the surface potential of the gamma-ray-irradiated poly-γ-glutamic acid hydrogel molecule was −35.18±1.72 mV.

As a result of calculating the number of free carboxyl groups remaining in the hydrogel using the measured surface potential, the number of free carboxyl groups in the UV-irradiated poly-γ-glutamic acid hydrogel was 4.5 μmol/g and the number of free carboxyl groups in the gamma-ray-irradiated poly-γ-glutamic acid hydrogel was 14 μmol/g.

TABLE 1

| sample | Surface potential (mV) | Number of free carboxyl groups (pH 4.8) |
|---|---|---|
| poly-γ-glutamic acid solution (1 μmol/ml) | −40.20 ± 0.33 | 0.5 μmol/ml |
| gamma-ray-irradiated poly-γ-glutamic acid hydrogel | −35.18 ± 1.72 | 14 μmol/g |
| UV-irradiated poly-γ-glutamic acid hydrogel | −29.30 ± 0.77 | 4.5 μmol/g |

As a result, it was confirmed that the UV-irradiated poly-γ-glutamic acid hydrogel was more crosslinked than the gamma-ray-irradiated poly-γ-glutamic acid hydrogel.

<Example 5> Confirmation of Stability in Solution

In order to confirm the stability in the solution of the poly-γ-glutamic acid hydrogel prepared by ultraviolet irradiation, the change in the shape of the hydrogel over time was confirmed together with the poly-γ-glutamic acid hydrogel irradiated with gamma rays.

3 g of UV-irradiated poly-γ-glutamic acid hydrogel was placed in a petri dish and air-dried to prepare a circular gel and distilled water, 20 mM potassium phosphate buffer (KPB; pH 6.0), 1×PBS, 0.9% sodium chloride (NaCl) solution and artificial body fluid were each poured so that the gel is immersed, and then allowed to stand at a humidity of 60% and a temperature of 25° C. to check the shape change.

In addition, $KH_2PO_4$ was added to a 5 w/v % solution of poly-γ-glutamic acid so as to be 0.1 w/v %, and gamma-ray irradiated poly-γ-glutamic acid hydrogel was prepared by irradiation with gamma radiation at a dose of 20 kGy, followed by freeze-drying to prepare powder and the powder was dissolved in distilled water to be 15 w/v % and 3 g of gamma-irradiated poly-γ-glutamic acid hydrogel was placed in a petri dish in the same manner as above, and distilled water, 20 mM potassium phosphate buffer (KPB; pH 6.0), 1×PBS, 0.9% sodium chloride (NaCl) solution and artificial body fluid were each poured so that the gel was immersed, and then allowed to stand at a humidity of 60% and a temperature of 25° C. to confirm the change in shape.

As a result, it was confirmed that the poly-γ-glutamic acid hydrogel prepared by ultraviolet irradiation as shown in FIG. 4 was maintained in shape for 8 weeks, whereas the poly-γ-glutamic acid hydrogel prepared by gamma ray irradiation was expanded and dissolved.

From the above results, it was confirmed that the poly-γ-glutamic acid hydrogel according to UV irradiation maintains stability for a long time even in a solution.

While the present invention has been particularly described with reference to specific embodiments thereof, it is apparent that this specific description is only a preferred embodiment and that the scope of the present invention is not limited thereby to those skilled in the art. That is, the practical scope of the present invention is defined by the appended claims and their equivalents.

The invention claimed is:

1. A method of preparing a biocompatible poly-γ-glutamic acid hydrogel comprising:
dissolving poly-γ-glutamic acid in a solvent (Step 1);
adding and dissolving N,N,N-trimethyl-3-[(2-methylacryloyl)amino]propane-1-aminium to solution of the poly-γ-glutamic acid of the Step 1 (Step 2); and
irradiating the solution of the Step 2 with ultraviolet rays (Step 3),
wherein the N,N,N-trimethyl-3-[(2-methylacryloyl)amino]propane-1-aminium in the Step 2 is added at a molecular ratio of 1:1 with respect to molecule number of glutamic acid, which is a poly-γ-glutamic acid monomer.

2. The method of preparing the biocompatible poly-γ-glutamic acid hydrogel of claim 1, wherein the poly-γ-glutamic acid has a weight average molecular weight of 30 to 30,000 kDa.

3. The method of preparing the biocompatible poly-γ-glutamic acid hydrogel of claim 1, wherein the solvent in the Step 1 is water.

4. The method of preparing the biocompatible poly-γ-glutamic acid hydrogel of claim 1, wherein in the Step 3 of irradiating ultraviolet rays, ultraviolet rays having an energy amount of 50 to 70 mW/cm$^2$ are irradiated to the solution of the Step 2.

5. The method of preparing the biocompatible poly-γ-glutamic acid hydrogel of claim 1, further comprising air-drying the solution irradiated with ultraviolet rays in the Step 3 at room temperature.

6. The method of preparing the biocompatible poly-γ-glutamic acid hydrogel of claim 1, wherein the poly-γ-glutamic acid hydrogel is contained in an artificial organ, tissue engineering scaffold, cosmetic material or a bio-ink composition for 3D printers with improved storage stability and viscoelasticity.

* * * * *